United States Patent [19]

Szum

[11] Patent Number: 5,384,342

[45] Date of Patent: Jan. 24, 1995

[54] VINYL ETHER URETHANE SILANES

[75] Inventor: David M. Szum, Marengo, Ill.

[73] Assignee: DSM Desotech, Inc., Elgin, Ill.

[21] Appl. No.: 113,997

[22] Filed: Aug. 30, 1993

[51] Int. Cl.$^6$ .............................. C07F 7/04; C07F 7/10; B32B 17/02; C09J 201/10

[52] U.S. Cl. ............................... 522/172; 522/173; 522/96; 556/52; 556/418; 556/419; 556/420; 428/447; 428/429; 428/378

[58] Field of Search ............ 522/99, 172, 173, 96; 428/447, 429, 378; 556/420, 419, 418, 52

[56] References Cited

U.S. PATENT DOCUMENTS

| | | | |
|---|---|---|---|
| 3,364,059 | 1/1968 | Marzocchi | 117/72 |
| 4,031,271 | 11/1975 | Bush | 427/43 |
| 4,567,107 | 1/1986 | Rizk et al. | 428/425.5 |
| 4,889,768 | 12/1989 | Yokoshima et al. | 556/420 |
| 5,039,716 | 8/1991 | Vara et al. | 522/172 |
| 5,220,047 | 6/1993 | Pohl et al. | 556/420 |

FOREIGN PATENT DOCUMENTS

| | | |
|---|---|---|
| 86-063160/10 | 3/1985 | European Pat. Off. . |
| 0298734 | 1/1989 | European Pat. Off. ............ 556/420 |
| 92-209647/26 | 12/1990 | European Pat. Off. . |
| 85-224098/37 | 2/1984 | Germany . |
| 86-131894/21 | 10/1984 | Germany . |
| 87-065752/10 | 8/1985 | Germany . |
| 87-109559/16 | 10/1985 | Germany . |
| 88-085250/13 | 9/1986 | Germany . |
| WO-9111-467-A | 1/1990 | Germany . |
| WO-9116-371-A | 8/1990 | Germany . |
| 026529/02 | 4/1977 | Japan . |
| 85-207804/34 | 12/1983 | Japan . |
| 87-140960/20 | 10/1985 | Japan . |
| 87-195207/28 | 11/1985 | Japan . |
| 0255289 | 10/1988 | Japan .................................. 556/420 |
| 90-325196/43 | 3/1989 | Japan . |
| 91-320266/44 | 1/1990 | Japan . |

Primary Examiner—Susan W. Berman
Attorney, Agent, or Firm—Dressler, Goldsmith, Shore & Milnamow, Ltd.

[57] ABSTRACT

The present invention is directed to a compound of the Formula:

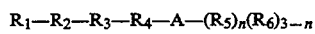

$$R_1-R_2-R_3-R_4-A-(R_5)_n(R_6)_{3-n}$$

wherein: A is Si or Ti; $R_1$ is an alkenoxy, acryloxy or ethylenically unsaturated dicarboxylate group; $R_2$ is a 2 to 18 carbon linear, branched or cyclo alkyl, alkenyl, alkynyl, acyl, aryl or poly(alkoxy) group; $R_3$ contains a urethane, urea, or thiourethane linkage; $R_4$ is a 2 to 18 carbon linear, branched, or cyclic alkyl, alkenyl, alkynyl, aryl or acyl non-hydrolyzable silyl linking group; $R_5$ is a 2 to 18 carbon linear, branched, or cyclic alkyl, alkenyl, alkynyl, aryl or acyl group; $R_6$ is any hydrolyzable silyl linking group (alkoxy, alkenoxy, or halogen); and n is 0 to 2.

The present invention is further directed to an improved method of using of a compound of the above Formula as an adhesion promoter in a UV-curable composition for a surface with a free nucleophilic group. Preferably, that surface is glass.

The present invention is yet further directed to an improved UV-curable coating composition, wherein the improvement comprises adding to said coating composition a compound of the above formula in an amount sufficient to promote adhesion of a coating to a surface with a free nucleophilic group.

8 Claims, No Drawings

VINYL ETHER URETHANE SILANES

DESCRIPTION

1. Field of the Invention

The present invention relates to an adhesion promoter, and more specifically to a vinyl ether urethane silane which promotes adhesion to glass and other surfaces.

2. Background of the Invention

Current adhesion promoters containing mercapto- and amine-functional silanes cause poor liquid stability and gelation in acrylate formulations at levels greater than 2 percent. At levels greater than 3 percent, most or all of the acrylate functionality in such acrylate formulations is reacted via conjugate addition, and the formulation is no longer UV curable.

Some currently available adhesion promoters contain UV curable groups which are attached to the silanes through a hydrolyzable linkage. This will lead to an adhesion promoter that is not long-lasting, as the polymer is attached to the substrate via a hydrolyzable linkage and activation of the silane requires hydrolysis.

It would thus be advantageous to have an adhesion promoter which could be used at levels above 1 to 2 percent, and which has a non-hydrolyzable linkage to promote greater efficiency and adhesion.

BRIEF SUMMARY OF THE INVENTION

The present invention is directed to a compound of the Formula I:

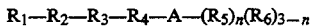

wherein:
A is Si or Ti;
$R_1$ is an alkenoxy, acryloxy or ethylenically unsaturated dicarboxylate group;
$R_2$ is a 2 to 18 carbon linear, branched or cyclo alkyl, alkenyl, alkynyl, acyl, aryl or poly(alkoxy) group;
$R_3$ contains a urethane, urea, or thiourethane linkage;
$R_4$ is a 2 to 18 carbon linear, branched, or cyclic alkyl, alkenyl, alkynyl, aryl or acyl non-hydrolyzable silyl linking group;
$R_5$ is a 2 to 18 carbon linear, branched, or cyclo alkyl, alkenyl, alkynyl, aryl or acyl group;
$R_6$ is any hydrolyzable silyl linking group such as alkoxy, alkenoxy, or halogen); and
and n is 0 to 2.
In a preferred embodiment,
A is Si;
$R_1$ is any UV-polymerizable functional group, such as an alkenoxy, acryloxy, and ethylenically unsaturated dicarboxylate;
$R_2$ is a 2 to 8 carbon linear, branched or cyclic alkyl, alkenyl, or poly(alkoxy) group;
$R_3$ is urethane or urea;
$R_4$ is a 2 to 6 carbon linear, branched or cyclic alkyl or alkenyl non-hydrolyzable silyl group;
$R_5$ is a 2 to 18 carbon linear, branched or cyclic alkyl, alkenyl, alkynyl or acyl group;
$R_6$ is a hydrolyzable silyl group such as alkoxy, alkenoxy, or halogen; and
n is 0 to 2.
In a more preferred embodiment,
A is Si;
$R_1$ is an alkenoxy group;
$R_2$ is butyl or 1,4-dimethylene cyclohexane;
$R_3$ is urethane;
$R_4$ is propyl; and
$R_5$ is ethoxy or methoxy.

In another embodiment, the present invention is directed to the compound of the Formula II

The present invention is still further directed to an improved method of using of a compound of the above Formula as an adhesion promoter in a UV-curable composition for a surface with a free nucleophilic group. Preferably, that surface is glass.

The present invention is yet further directed to an improved UV-curable coating composition, wherein the improvement comprises adding to said coating composition a compound of the above formula in an amount sufficient to promote adhesion of a coating to a surface with a free nucleophilic group.

DETAILED DESCRIPTION OF THE INVENTION

The present invention is directed to a compound of the Formula:

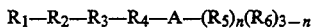

wherein:
A is Si or Ti;
$R_1$ is an alkenoxy, acryloxy or ethylenically unsaturated dicarboxylate group;
$R_2$ is a 2 to 18 carbon linear-, branched- or cyclic-alkyl, alkenyl, alkynyl, acyl, aryl or poly(alkoxy) group;
$R_3$ is urethane, urea, or thiourethane;
$R_4$ is a 2 to 18 carbon linear-, branched-, or cyclic-alkyl, alkenyl, alkynyl, aryl or acyl nonhydrolyzable silyl group;
$R_5$ is a 2 to 18 carbon linear-, branched-, or cyclic-alkyl, alkenyl, alkynyl, aryl or acyl group;
$R_6$ is any hydrolyzable silyl group such as alkoxy, alkenoxy, or halogen; and
n is 0 to 2.

"Alkenoxy" as used herein refers to the group R—CH═CH—O— where R is H, $CH_3$ or $CH_2CH_3$. Exemplary alkenoxy groups include ethenoxy, propenoxy, butenoxy, and all structural and geometrical isomers thereof.

"Acryloxy" as used herein is synonymous with acrylyoxy, and refers to the group $CH_2{:}CHCO_2$—.

"Ethylenically unsaturated dicarboxylate" as used herein means a dicarboxylate carrying an ethylene unsaturation. Exemplary ethylenically unsaturated dicarboxylates are maleates and fumarates.

"Alkyl" as used herein means a saturated aliphatic hydrocarbon group. Exemplary alkyl groups have 2 to about 18 carbon atoms and may be ethyl, propyl, butyl, pentyl, hexyl, heptyl, octyl, nonyl, decyl, undecyl, dodecyl, tridecyl, tetradecyl, pentadecyl, hexadecyl, heptadecyl, and octadecyl, including all structural and geometrical isomers thereof.

"Cyclicalkyl" as used herein means a saturated cyclic hydrocarbon group. Exemplary cyclicalkyl groups have 3 to about 18 carbon atoms and may be cyclopropyl, cyclohexyl, cyclononyl, cyclopentadecyl, and cyclooctadecyl, and all structural and geometrical isomers thereof.

"Alkenyl" as used herein means an unsaturated aliphatic hydrocarbon group containing a double bond. Exemplary alkenyl groups having 2 to about 18 carbon atoms include ethylenyl, propylenyl, butylenyl, isobutylenyl, dodecylenyl, and octadecylenyl, and all structural and geometrical isomers thereof.

"Aryl" as used herein means aromatic rings that are fused, unfused or linked and can include one or more heteroatoms, as for example, phenyl, naphthyl, anthracenyl, biphenyl, quinolyl and the like.

"Cyclicalkenyl" as used herein means an unsaturated monocylic hydrocarbon containing a double bond. Exemplary cyclicalkenyl groups having 3 to about 18 carbon atoms include cyclopenytynyl, cycolbutylenyl, cyclododecylenyl, and cyclooctadecynyl, and all structural and geometrical isomers thereof.

"Alkynyl" as used herein means an unsaturated aliphatic hydrocarbon containing a triple bond. Exemplary alkynyl groups having 2 to about 18 carbon atoms include ethylynyl, propylynyl, butylynyl, isobutylynyl, dodecylynyl, and octadecylynyl and all structural and geometrical isomers thereof.

"Cyclicalkynyl" as used herein means an unsaturated monocyclic hydrocarbon containing a triple bond. Exemplary alkynyl groups having 2 to about 18 carbon atoms include cyclopropylynyl, cyclobutylynyl, cycloisobutylynyl, cyclododecylynyl, and cyclooctadecylynyl and all structural and geometrical isomers thereof.

"Acyl" as used herein means the functional group when the hydroxyl group of the corresponding acid is removed. Exemplary acyl groups include methanoyl, propanoyl, isobutanoyl, octanoyl, and octadecanoyl, and all structural and geometrical isomers thereof.

"Cyclicacyl" as used herein means a monocyclic acyl group. Exemplary cyclicacyl groups include cyclohexanecarbanoyl and cyclopropanecarbanoyl, and all structural and geometrical isomers thereof.

"Poly(alkoxy)" as used herein means repeating units of alkoxy groups. An alkoxy group is that which remains when the hydrogen attached to an alcohol is removed. Exemplary alkoxy groups are methoxy, isopropoxy, octoxy, dodecoxy, and all structural and geometrical isomers thereof.

"Cyclic-poly(alkoxy)" as used herein means repeating units of cycloalkoxy groups. Exemplary cycloalkoxy groups are cyclodecoxy, cycloheptoxy, cyclohexoxy, and all structural and geometrical isomers thereof.

"Non-hydrolyzable silyl group" as used herein means a silyl group which cannot be hydrolyzed. Exemplary non-hydrolyzable silyl groups are those in which silane is covalently bonded to a linear-, branched- or cyclic-alkyl, alkenyl, alkynyl, or acyl group.

"Hydrolyzable silyl group" as used herein means a silyl group which can be hydrolyzed. Exemplary hydrolyzable silyl groups are those in which silane is covalently bonded to an alkoxy, alkenoxy, or halogen group.

In a preferred embodiment,
A is Si;
R₁ is any UV-polymerizable functional group, such as an alkenoxy, acryloxy, or ethylenically unsaturated dicarboxylate group;
R₂ is a 2 to 8 carbon linear, branched or cyclic alkyl, alkenyl, or poly(alkoxy) group;
R₃ is urethane or urea;
R₄ is a 2 to 6 carbon linear, branched or cyclic alkyl or alkenyl non-hydrolyzable silyl group;
R₅ is a 2 to 18 carbon linear, branched or cyclic alkyl, alkenyl, alkynyl or acyl group;
R₆ is independently a hydrolyzable silyl group such as alkoxy, alkenoxy, or halogen; and
n is 0 to 2.

In a more preferred embodiment,
A is Si;
R₁ is an alkenoxy group;
R₂ is butyl or 1,4-dimethylene cyclohexane;
R₃ is urethane;
R₄ is propyl; and
R₆ is ethoxy or methoxy.

Representative silanes of the present invention include silanes of Formula III through VII as follows:

III

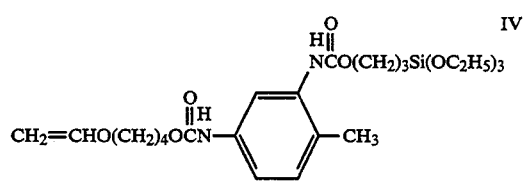

IV

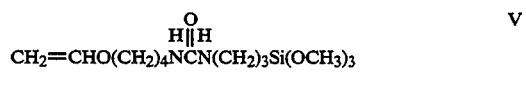

V

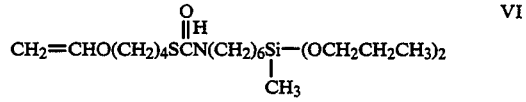

VI

VII

The present invention is still further directed to an improved method of using a compound of the above Formula as an adhesion promoter in a UV-curable coating composition for a surface with a free nucleophilic group.

An adhesion promoter acts to enhance the adhesion of an optical fiber primary coating to materials with a free nucleophilic group. A free nucleophilic group is a group capable of donating an electron pair, i.e., a Lewis base. Exemplary nucleophilic groups include silanol, hydroxyl and amine groups.

Preferably, the surface with a free nucleophilic group is glass. In particular, the adhesion promoter can be used on optical glass fiber, on fiberglass insulation, and on glass bottles.

The composition of the present invention is also useful as an adhesion promoter for wood, metal, polycarbonates, and polyacrylic surfaces, which surfaces also carry nucleophilic groups.

The UV curable coating composition has the characteristics typical for the particular use the coating composition will ultimately have. For example, if the UV curable coating composition is to coat the glass surface of an optical fiber, the coating composition should cure on radiation exposure to have a room temperature tensile modulus which is low enough to minimize the danger of microbending at reduced temperatures.

Radiation curable coating compositions can be of various types, again depending on the application. For coating glass optical fibers, a polyethylenic polymeric compound is appropriate. Exemplary coatings of this type are disclosed in Ansel, U.S. Pat. No. 4,624,994.

One illustrative UV-curable coating composition is a mixture of acrylate-capped polyurethane oligomer with N-vinyl pyrrolidone and phenoxyethyl acrylate. This mixture, with 3% of diethoxy acetophenone as a photoinitiator, can be ultravioletly cured on freshly drawn optical glass fiber, and it can be modified to enhance retention of adhesion to the glass according to the methods of the present invention.

Other suitable UV photoinitiators include acetophenone, benzophenone, m-chloro-acetophenone, propiophenone, thioxanthone, benzoin, benzil, anthraquinone, and the like.

The present invention is yet further directed to an improved UV-curable coating, wherein the improvement comprises adding a compound of the above formula in an amount sufficient to promote adhesion of a coating to a surface with a free nucleophilic group.

The composition of the present invention are preferably used in UV-curable formulations in amounts from about 0.01 to about 50 weight percent, or more preferably from about 0.1 to about 30 weight percent of the total weight of the composition. The amount of the composition of the present invention needed in any particular adhesion formulation can be readily determined by those of ordinary skill in the art.

The following examples further illustrate the invention and are not to be construed as limiting of the specification and claims in any way.

EXAMPLE 1

4-Ethenoxybutyl-3-(Triethoxysilano) Propyl Carbamate

Gamma isocyanoto propyl triethoxy silane (A-1310; 106.21 g), dibutyl tin dilaurate (DBTDL; 0.10 g), and butylated hydroxytoluene (BHT; 0.05%) were charged into a 4-neck 500 ml flask. Hydroxybutyl vinyl ether (HBVE; 43.3 g) was then added slowly over the next hour. The reaction mixture was then held at 60° C. for 2 hours. The reaction yielded the title compound.

EXAMPLE 2

6-Ethenoxyhexyl-3-(Triethoxysilano) Propyl Carbamate

A-1310, DBTL, and BHT were added to a four neck flask fitted with an agitator, a condenser, a sparge line, and a thermocouple. The reaction mixture was heated to 40° C. with agitation and low dry air sparge. Hexane diol monovinyl ether was then slowly added over the next hour. The temperature of the reaction mixture was then increased to 60° C. for one hour.

The reaction mixture was sampled for isocyanate content to see if it reached a value of less than 0.1 weight percent. If it had not, the reaction mixture was maintained at 60° C. for another hour. If the value of the isocyanate was still greater than 0.1 weight percent, a stoichiometric amount of hexane diol monovinyl ether was added to the reaction. The reaction was continually monitored for isocyanate levels, with hexane diol monovinyl ether being added as described until the isocyanate levels were under 0.1.

EXAMPLE 3

N-(3-Ethenoxypropyl)-N'-[3-Triethoxysilanopropyl]urea

A-1310, DBTDL and BHT were added to a four neck flask fitted as described in Example 2, and the reaction mixture was heated to 40° C. with agitation and sparge. Amino propyl vinyl ether was then added slowly over the next hour. The temperature of the reaction mixture was then raised to 60° C. and held there for one hour.

The reaction mixture was sampled for isocyanate to see if it reached a value of less than 0.1 weight percent. If it had not, the reaction mixture was maintained at 60° C. for another hour. If the value of the isocyanate was still greater than 0.1 weight percent, a stoichiometric amount of amino propyl vinyl ether was added to the reaction. The reaction was continually monitored for isocyanate levels, with amino propyl vinyl ether being added as described until the isocyanate levels were under 0.1 weight percent.

EXAMPLE 4

Effectiveness of Adhesion Promoters

Various adhesion promoter formulations were examined for their tensile strength, elongation, and modulus. The initial adhesion and wet adhesion of these formulations was also compared. The data are presented in Table 1; the values of the components of the various formulations are all listed in weight percent.

TABLE 1

| | Formulation Number and Weight Percent of Components | | | | | | |
|---|---|---|---|---|---|---|---|
| | CONTROL[4] | I | II | III | IV | V | VI |
| Oligomer | 60 | | | | | | |
| Ethoxylated Nonyl Phenyl Acrylate | 33 | | | | | | |
| Phenoxy Ethyl Acrylate | 5 | | | | | | |
| Triphenyl Phosphine Oxide[1] | 1.5 | | | | | | |
| Gamma-Mercapto Propyl Trimethoxy Silane | | | | | | | 1 |
| Vinyl Ether Urethane Silane[2] | | 1 | 5 | 10 | 20 | 30 | |
| Irganox 1010[3] | .5 | | | | | | |
| Control Formulation | | 99 | 95 | 90 | 80 | 70 | 99 |
| Tensile (mPa) | 1.3 | 1.2 | 1.5 | 1.6 | 1.6 | 0.8 | 1.3 |
| Elongation (%) | 95 | 85 | 70 | 54 | 41 | 45 | 110 |
| Modulus (mPa) | 2.4 | 2.6 | 3.5 | 4.2 | 4.8 | 2.5 | 2.3 |
| Adhesion* | 13 | 30 | 62 | 76 | *** | *** | 34 |
| Wet Adhesion** | 2 | 20 | 43 | 61 | *** | *** | 25 |

*Initial Adhesion at 23° C. and 50% relative adhesion.
**23° C., 95% relative humidity.
***These samples were of such high adhesion that the samples tore apart during the adhesion test rather than peeling off the glass.
Footnotes:
[1]Photoinitiator
[2]Vinyl ether urethane silane of Example 1
[3]Antioxidant
[4]Contains no adhesion promotor Adhesion is determined using glass plates as above and test specimens are prepared by making six-inch cuts in the cured film. A thin layer of talc is applied to the first and third strips of each drawdown. The end of the first strip is pulled back from the glass plate about one-inch and the Instron Model 4201 is used by attaching the binder clip to the pulled back end of the specimen. When the average force value becomes relatively constant, the mean adhesion value in grams force/inch is calculated.

Formulation Number VI represents current technology. When compared to Formulation Number I, in which the equivalent weight percent of the compound prepared in Example 1 is present, the two materials perform equally well.

The advantage of the use of a compound of the instant invention in these formulations is that higher levels of that compound can be used, as illustrated by Formulation Numbers II–V. A-189 can be used at an approximate 2 weight percent level before film integrity is lost due to loss of acrylate functionality. In contrast, use of 30 weight percent of the compound prepared in Example 1 provides such high adhesion that the glass samples tore apart before the film peeled off, when measured in the adhesion test.

The foregoing specification, including the specific embodiments and examples is intended to be illustrative of the present invention and is not to be taken as limiting. Numerous other variations and modifications can be effected without departing from the true spirit and scope of the present invention.

I claim:

1. A compound of the Formula:

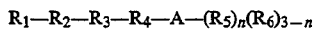

I wherein:

A is Si or Ti;

$R_1$ is an alkenoxy, or ethylenically unsaturated dicarboxylate group;

$R_2$ is a 2 to 18 carbon linear, branched or cyclic alkyl, alkenyl, alkynyl, acyl, aryl or poly(alkoxy);

$R_3$ contains a urethane, urea, or thiourethane linkage;

$R_4$ is a 2 to 18 carbon linear, branched, or cyclic alkyl, alkenyl, alkynyl, aryl or acyl non-hydrolyzable silyl linking group;

$R_5$ is a 1 to 18 carbon linear, branched, or cyclic alkyl, alkenyl, alkynyl, aryl or acyl;

$R_6$ is 2 to 18 carbon alkoxy or alkenoxy, or halogen; and n is 0 to 2.

2. The compound of claim 1 wherein

A is Si;

$R_1$ is an alkenoxy, or ethylenically unsaturated dicarboxylate group;

$R_2$ is a 2 to 8 carbon linear, branched or cyclic alkyl, alkenyl, or poly(alkoxy) group;

$R_3$ is urethane or urea;

$R_4$ is a 2 to 6 carbon linear, branched or cyclic alkyl or alkenyl group;

$R_5$ is a 2 to 18 carbon linear, branched or cyclic alkyl, alkenyl, alkynyl or acyl group;

$R_6$ is alkoxy, alkenoxy, or halogen; and n is 0 to 2.

3. The compound of claim 1 wherein

A is Si;

$R_1$ is an alkenoxy group;

$R_2$ is butyl or 1,4-dimethylene cyclohexane;

$R_3$ is urethane;

$R_4$ is propyl; and $R_5$ is ethoxy or methoxy.

4. The compound

5. An improved UV-curable coating composition wherein the improvement comprises adding to said composition a compound of claim 1 in an amount sufficient to promote adhesion of a coating to a surface with a free nucleophilic group.

6. The UV-curable coating composition of claim 5 wherein said compound is present in an amount from 0.01 to about 50 weight percent of the total weight of said composition.

7. The UV-curable coating composition of claim 5 wherein said compound is present in an amount from 0.1 to about 30 weight percent of the total weight of said composition.

8. The UV-curable coating composition of claim 5 wherein said surface is glass.

* * * * *